(12) United States Patent
Olson et al.

(10) Patent No.: US 9,114,232 B2
(45) Date of Patent: Aug. 25, 2015

(54) CATHETER FOR MANUAL AND REMOTE MANIPULATION

(71) Applicant: St. Jude Medical, Atrial Fibrillation Division, Inc., St. Paul, MN (US)

(72) Inventors: Eric S. Olson, Maplewood, MN (US); Mark B. Kirschenman, Waverly, MN (US)

(73) Assignee: St. Jude Medical, Atrial Fibrillation Division, Inc., St. Paul, MN (US)

( * ) Notice: Subject to any disclaimer, the term of this patent is extended or adjusted under 35 U.S.C. 154(b) by 84 days.

(21) Appl. No.: 13/729,981

(22) Filed: Dec. 28, 2012

(65) Prior Publication Data

US 2013/0172814 A1 Jul. 4, 2013

Related U.S. Application Data

(60) Provisional application No. 61/581,880, filed on Dec. 30, 2011.

(51) Int. Cl.
*A61M 25/01* (2006.01)
(52) U.S. Cl.
CPC ....... *A61M 25/0147* (2013.01); *A61M 25/0113* (2013.01); *A61M 25/0136* (2013.01); *A61M 25/0155* (2013.01)
(58) Field of Classification Search
CPC ..................... A61M 25/0155; A61M 25/0113; A61M 25/0147; A61M 25/0105; A61M 25/0136
USPC ..................................... 604/95.04; 606/130, 1
See application file for complete search history.

(56) References Cited

U.S. PATENT DOCUMENTS

| | | | |
|---|---|---|---|
| 6,183,444 B1 * | 2/2001 | Glines et al. .................. | 604/187 |
| 6,233,476 B1 | 5/2001 | Strommer et al. | |
| 6,498,944 B1 | 12/2002 | Ben-Haim et al. | |
| 6,690,963 B2 | 2/2004 | Ben-Haim et al. | |
| 6,788,967 B2 | 9/2004 | Ben-Haim et al. | |
| 7,197,354 B2 | 3/2007 | Sobe | |
| 7,263,397 B2 | 8/2007 | Hauck et al. | |
| 7,386,339 B2 | 6/2008 | Strommer et al. | |
| 2007/0198008 A1 * | 8/2007 | Hauck et al. .................... | 606/41 |
| 2008/0103491 A1 * | 5/2008 | Omori et al. ...................... | 606/1 |
| 2009/0247942 A1 | 10/2009 | Kirschenman | |
| 2009/0247943 A1 | 10/2009 | Kirschenman | |
| 2009/0247944 A1 | 10/2009 | Kirschenman | |
| 2009/0247993 A1 * | 10/2009 | Kirschenman et al. ........... | 606/1 |

(Continued)

FOREIGN PATENT DOCUMENTS

WO WO2009120982 10/2009

*Primary Examiner* — Theodore Stigell
(74) *Attorney, Agent, or Firm* — Dykema Gossett PLLC (57) ABSTRACT

An elongate medical device may overcome be configured both for manual manipulation by a physician and for automatic manipulation by a remote catheter guidance system. Such an elongate medical device comprises a shaft having a proximal portion and a distal portion, a pull wire disposed in the shaft and affixed to the distal portion of the shaft, and a handle coupled with the proximal portion of the catheter shaft. The handle comprises a first mechanism configured for manual actuation of the pull wire so as to deflect the distal portion of the shaft, a second mechanism configured for remote actuation of the pull wire so as to deflect the distal portion of the shaft, and a mechanical interface configured to provide a remote catheter guidance system with a functional connection to the second mechanism.

20 Claims, 6 Drawing Sheets

(56) References Cited

U.S. PATENT DOCUMENTS

| | | |
|---|---|---|
| 2009/0248042 A1 | 10/2009 | Kirschenman |
| 2010/0256558 A1 | 10/2010 | Olson et al. |
| 2011/0015569 A1 | 1/2011 | Kirschenman et al. |
| 2012/0197190 A1* | 8/2012 | Suon et al. ............... 604/95.04 |
| 2012/0303006 A1* | 11/2012 | Lee et al. ..................... 606/1 |

* cited by examiner

CATHETER FOR MANUAL AND REMOTE MANIPULATION

CROSS-REFERENCE TO RELATED APPLICATION

This application claims priority to U.S. provisional patent application No. 61/581,880, filed Dec. 30, 2011, which is hereby incorporated by reference in its entirety as though fully set forth herein.

BACKGROUND OF THE INVENTION a. Field of the Invention

The instant disclosure relates generally to elongate medical devices for use with a remote catheter guidance system (RCGS), including elongate medical devices suitable for both manual use and automated use with an RCGS.

b. Background Art

It is known to use electrophysiology (EP) catheters for a variety of diagnostic and/or therapeutic medical procedures to correct conditions such as atrial arrhythmia, including for example, ectopic atrial tachycardia, atrial fibrillation, and atrial flutter. Arrhythmia can create a variety of dangerous conditions including irregular heart rates, loss of synchronous atrioventricular contractions and stasis of blood flow which can lead to a variety of ailments.

In a typical EP procedure, a physician manipulates a catheter through a patient's vasculature to, for example, a patient's heart. The catheter typically carries one or more electrodes that may be used for mapping, ablation, diagnosis, and the like. Once at the target tissue site, the physician commences diagnostic and/or therapeutic procedures, for example, ablative procedures such as radio frequency (RF), microwave, cryogenic, laser, chemical, acoustic/ultrasound or high-intensity focused ultrasound (HIFU) ablation, to name a few different sources of ablation energy. The resulting lesion may disrupt undesirable electrical pathways and thereby limit or prevent stray electrical signals that can lead to arrhythmias. Such procedures can require precise control of the catheter during navigation to and delivery of therapy to the target tissue site.

Robotic catheter systems are known to facilitate precise control. Robotic catheter systems generally carry out (as a mechanical surrogate) input commands of a clinician or other end-user to deploy, navigate and manipulate a catheter and/or an introducer or sheath for a catheter or other elongate medical instrument, for example, a robotic catheter system described, depicted, and/or claimed in U.S. patent application Ser. No. 12/347,811 entitled "ROBOTIC CATHETER SYSTEM," hereby incorporated by reference in its entirety as though fully set forth herein. Such robotic catheter systems include a variety of actuation mechanisms, such as electric motors, for controlling translation and deflection of the catheter and associated sheath.

A variety of catheter form factors for robotic manipulation and associated robotic actuation mechanisms are known. For example, as described in the above-referenced U.S. patent application Ser. No. 12/347,811, a catheter may be provided in a cartridge specifically designed for use with a robotic system. The robotic system, in turn, may contain a manipulation structure specifically designed for use with the catheter cartridge form factor. However, such a catheter cartridge can be more difficult to guide manually than a traditional manual catheter handle. In another example, such as disclosed in U.S. Patent Application Publication No. 2007/0198008, entitled "ROBOTIC SURGICAL SYSTEM AND METHOD FOR AUTOMATED THERAPY DELIVERY," hereby incorporated by reference in its entirety, a traditional manual catheter handle may be controlled by a robotic manipulator manipulating the same actuation mechanisms that a physician would manipulate during manual use. Although such a system allows for robotic and manual manipulation of the same catheter form factor, it can require that the robotic manipulator be specifically designed to manipulate the manual catheter steering mechanism. Because different manual catheter handles may have different types, numbers, and placements of steering mechanisms, the use of such a robotic system may be limited by the design of the manipulator mechanism.

There is therefore a need for an improved interface for coupling a catheter to a RCGS while allowing a high degree of manual manipulation of the catheter by a physician.

BRIEF SUMMARY OF THE INVENTION

An elongate medical device may overcome some disadvantages of the prior art by being configured both for manual manipulation by a physician and for automatic manipulation by a remote catheter guidance system. Such an elongate medical device comprises a shaft having a proximal portion and a distal portion, a pull wire disposed in the shaft and affixed to the distal portion of the shaft, and a handle coupled with the proximal portion of the catheter shaft. The handle comprises a first mechanism configured for manual actuation of the pull wire so as to deflect the distal portion of the shaft, a second mechanism configured for remote actuation of the pull wire so as to deflect the distal portion of the shaft, and a mechanical interface configured to provide a remote catheter guidance system with a functional connection to the second mechanism.

The second actuation mechanism—i.e., the mechanism for remote actuation—may take a number of forms in different embodiments. In an embodiment, the second mechanism is hydraulic. An embodiment of the hydraulic mechanism comprises a drive cylinder, a hydraulic fluid line, a drive shaft coupled with the drive cylinder and coupled with the pull wire through an anchor block. The hydraulic fluid line may be coupled at a first end with the drive cylinder and at a second end with the interface and can be configured to provide hydraulic fluid to the drive cylinder. In an embodiment, the first actuation mechanism may also be coupled with the anchor block. The interface may comprise a hydraulic fluid port coupled with the hydraulic fluid line and a valve configured to selectively permit said remote system access to said hydraulic fluid line or to seal said hydraulic fluid line, in an embodiment.

In a further embodiment of the elongate medical device, the medical device may further comprise a force translation mechanism configured to translate force on the second mechanism into actuation of the pull wire. In an embodiment, the second actuation mechanism can comprise a socket. In the same or another embodiment, the force translation mechanism may comprise one or more mechanisms selected from the group consisting of gears, pulleys, wires, cables, and levers.

In an embodiment including a socket as the second actuation mechanism, the pull wire may be a first pull wire configured to deflect the distal portion in a first deflection direction in response to torque on the socket in a first rotational direction, and the medical device may further comprise a second pull wire configured to deflect the distal portion in a second deflection direction opposite the first deflection direction in response to torque on the socket in a second rotational direction opposite the first rotational direction. In a further embodiment, the socket may comprise a first socket and the medical device may further comprise a third pull wire and a second socket coupled to the third pull wire. The third pull wire may be configured to deflect the distal portion in a third deflection direction, for example, substantially orthogonal to the first and second directions in response to torque on the second socket.

The elongate medical device may also include various other features. In an embodiment, the elongate medical device may comprise a sensor configured to determine the position of the pull wire. In the same or another embodiment, the medical device may further comprise an irrigation fluid pathway extending through the shaft and terminating at the mechanical interface.

Another embodiment of an elongate medical device configured for manual use and for remote manipulation may comprise a modular configuration. Such an elongate medical device may comprise a modular cartridge and a handle portion releasably coupled with the modular cartridge. The modular cartridge may comprise a housing, a shaft having a distal portion and a proximal portion, the proximal portion coupled with the housing, a pull wire extending through the shaft and coupled with the distal portion of the shaft, and an interface member movably disposed within the housing, said interface member coupled with said pull wire such that movement of said interface member results in movement of the pull wire. The handle portion can comprise a receiving member releasably coupled with the interface member, and an actuation mechanism configured for manual manipulation, coupled with the receiving member, configured to impart force to the pull wire through the receiving member so as to deflect the distal portion of the shaft.

In an embodiment, the modular cartridge may further comprise a connection interface comprising an irrigation fluid port. In a further embodiment, the modular cartridge connection interface can further comprise at least one electrical connection for electrically coupling the handle portion with a sensor disposed in the shaft. In a still further embodiment, the handle portion may further comprise a handle portion fluid interface and a handle portion electrical interface. In an embodiment, the modular cartridge housing may be substantially round. In an embodiment, the modular cartridge may further comprise a sensor configured to sense the position of said connection member.

Another embodiment of an elongate medical device configured for manual use and for remote manipulation may comprise a shaft having a proximal portion and a distal portion, a pull wire disposed in the shaft and affixed to the distal portion of the shaft, and a handle having a distal end and a proximal end, the distal end coupled with the proximal portion of the catheter shaft. The proximal end of the handle may comprise an interface for coupling with a remote catheter guidance system, the interface comprising at least one electrical connector, a fluid port, a mechanical interlock, and an apparatus for actuating the pull wire so as to deflect the distal portion of the catheter shaft. In an embodiment, the apparatus for actuating the pull wire can comprise one or more of a hydraulic fluid port and a socket.

DETAILED DESCRIPTION OF THE INVENTION

Figure 1:
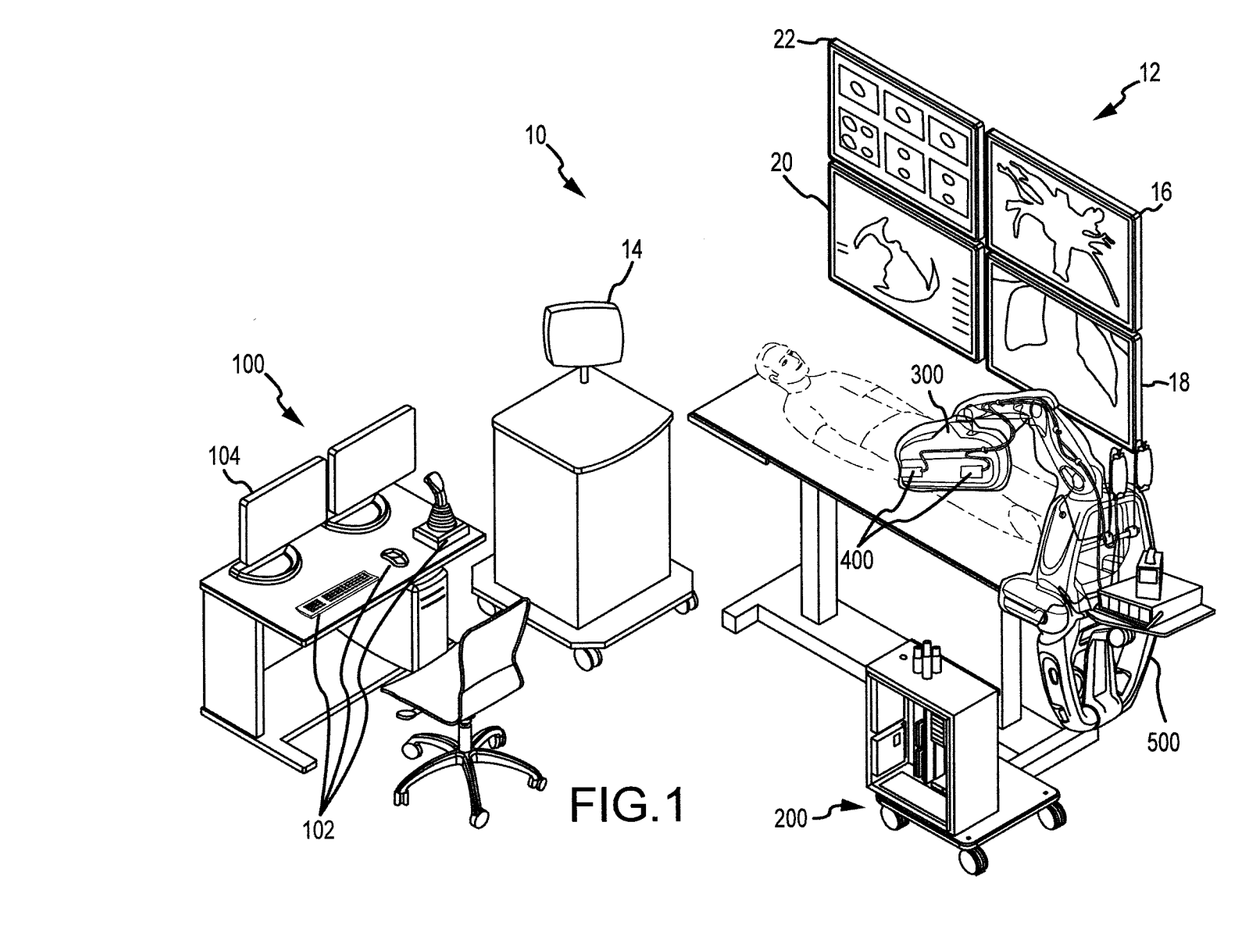
FIG. 1 is an isometric diagrammatic view of a robotic catheter system, illustrating an exemplary layout of various system components.

Referring now to the drawings wherein like reference numerals are used to identify the same or substantially similar components in the various views, FIG. 1 illustrates one exemplary embodiment of a robotic control and guidance system 10 (RCGS 10) for manipulating one or more medical devices. The RCGS 10 can be used, for example, to manipulate the location and orientation of catheters and sheaths in a heart chamber or in another body cavity or lumen. The RCGS 10 thus provides the user with a similar type of control provided by a conventional manually-operated system, but allows for repeatable, precise, and dynamic movements. For example, a user such as a physician or electrophysiologist can identify locations (potentially forming a path) on a rendered computer model of the cardiac anatomy. The system can be configured to relate those digitally selected points to positions within a patient's actual/physical anatomy, and can thereafter command and control the movement of the sheath and/or catheter to the defined positions. Once at a specified target position, either the user or the system can perform the desired diagnostic or therapeutic function. The RCGS 10 can enable full robotic navigation/guidance and control.

As shown in FIG. 1, the RCGS 10 can generally include one or more monitors or displays 12, a visualization, mapping, and/or navigation system 14, a human input device and control system (referred to as "input control system") 100, an electronic control system 200, a manipulator assembly 300 for operating one or more device cartridges 400, and a manipulator support structure 500 for positioning the manipulator assembly 300 in proximity to a patient or a patient's bed.

The displays 12 can be configured to visually present a user with information regarding patient anatomy, medical device location or the like, originating from a variety of different sources. The displays 12 can include, for example, (1) a monitor 16 (coupled to system 14—described more fully below) for displaying cardiac chamber geometries or models, displaying activation timing and voltage data to identify arrhythmias, and for facilitating guidance of catheter movement; (2) a fluoroscopy monitor 18 for displaying a real-time x-ray image or for assisting a physician with catheter movement; (3) an intra-cardiac echo (ICE) display 20 to provide further imaging; and/or (4) an EP recording system display 22.

The visualization, navigation, and/or mapping system 14 may be configured to provide a number of advanced features, such as visualization, mapping, navigation support and positioning (i.e., determine a position and orientation (P&O) of a sensor-equipped medical device, for example, a P&O of a distal tip portion of a catheter). In an exemplary embodiment, the system 14 may comprise an impedance-based system, such as, for example, the EnSite NavX™ system commercially available from St. Jude Medical, Inc., and as generally disclosed in U.S. Pat. No. 7,263,397 entitled "Method and Apparatus for Catheter Navigation and Location and Mapping in the Heart," the entire disclosure of which is incorporated herein by reference. In other exemplary embodiments, however, the system 14 may comprise other types of systems, such as, for example and without limitation: a magnetic-field based system such as the Carto™ System available from Biosense Webster, and as generally shown with reference to one or more of U.S. Pat. No. 6,498,944 entitled "Intrabody Measurement," U.S. Pat. No. 6,788,967 entitled "Medical Diagnosis, Treatment and Imaging Systems," and U.S. Pat. No. 6,690,963 entitled "System and Method for Determining the Location and Orientation of an Invasive Medical Instrument," the entire disclosures of which are incorporated herein by reference, or the gMPS system from MediGuide Ltd., and as generally shown with reference to one or more of U.S. Pat. No. 6,233,476 entitled "Medical Positioning System," U.S. Pat. No. 7,197,354 entitled "System for Determining the Position and Orientation of a Catheter," and U.S. Pat. No. 7,386,339 entitled "Medical Imaging and Navigation System," the entire disclosures of which are incorporated herein by reference; and a combination impedance-based and magnetic field-based system such as the Carto 3 System also available from Biosense Webster.

As briefly described above, in an exemplary embodiment, the system 14 involves providing one or more positioning sensors for producing signals indicative of medical device location (position and/or orientation) information. In an embodiment wherein the system 14 is an impedance-based system, the sensor(s) may comprise one or more electrodes. Alternatively, in an embodiment wherein the system 14 is a magnetic field-based system, the sensor(s) may comprise one or more magnetic sensors (e.g., coils) configured to detect one or more characteristics of a low-strength magnetic field.

The input control system 100 may be configured to allow a user, such as an electrophysiologist, to interact with the RCGS 10, in order to control the movement and advancement/withdrawal of one or more medical devices, such as, for example, a catheter and/or a sheath (see, e.g., U.S. Patent Publication No. 2010/0256558 entitled "Robotic Catheter System," and PCT/US2009/038597 entitled "Robotic Catheter System with Dynamic Response," published as WO 2009/120982, the entire disclosures of which are incorporated herein by reference). Generally, several types of input devices and related controls can be employed, including, without limitation, instrumented traditional catheter/sheath handle controls, oversized catheter/sheath models, instrumented user-wearable gloves, touch screen display monitors, 2-D input devices, 3-D input devices, spatially detected styluses, and traditional joysticks. For a further description of exemplary input apparatus and related controls, see, for example, U.S. Patent Publication Nos. 2011/0015569 entitled "Robotic System Input Device" and 2009/0248042 entitled "Model Catheter Input Device," the entire disclosures of which are incorporated herein by reference. The input devices can be configured to directly control the movement of the catheter and sheath, or can be configured, for example, to manipulate a target or cursor on an associated display.

The electronic control system 200 can be configured to translate (i.e., interpret) inputs (e.g., motions) of the user at an input device of the input control system 100 (or from another source) into a resulting movement of one or more medical devices (e.g., a catheter and/or a sheath). In this regard, the system 200 may include a programmed electronic control unit (ECU) in communication with a memory or other computer readable media (memory) suitable for information storage. Relevant to the present disclosure, the electronic control system 200 may be configured, among other things, to issue commands (i.e., actuation control signals) to the manipulator assembly 300 (i.e., to the actuation units—electric motors thereof, in particular) to move or deflect the medical device(s) associated therewith to prescribed positions and/or in prescribed ways, all in accordance with the received user input and/or a predetermined operating strategy programmed into the system 200. In addition to the instant description, further details of a programmed electronic control system can be found in U.S. Patent Publication No. 2010/0256558, the entire disclosure of which was incorporated herein by reference above. It should be understood that although the visualization, navigation, and/or mapping system 14 and the electronic control system 200 are shown separately in FIG. 1, integration of one or more computing functions can result in a system including an ECU on which can be run both (i) various control and diagnostic logic pertaining to the RCGS 10 and (ii) the visualization, navigation, and/or mapping functionality of system 14.

The manipulator assembly 300, in response to commands issued by the electronic control system 200, can be configured to maneuver the medical device(s) associated therewith (e.g., translation movement, such as advancement and withdrawal of the medical device(s)), as well as to effectuate distal end (tip) deflection and/or rotation or virtual rotation. In an embodiment, the manipulator assembly 300 can include actuation mechanisms/units (e.g., a plurality of electric motor and lead screw combinations, or other electric motor configurations) for linearly actuating one or more control members (e.g., steering wires) associated with the medical device(s) for achieving the above-described translation, deflection and/or rotation (or virtual rotation). In addition to the description set forth herein, further details of a manipulator assembly can be found in U.S. Patent Publication No. 2009/0247942 entitled "Robotic Catheter Manipulator Assembly," the entire disclosure of which is incorporated herein by reference.

A device cartridge 400 can be provided for each medical device controlled by the RCGS 10. For this exemplary description of an RCGS, and as will be described in greater detail below, one cartridge may be associated with a catheter and a second cartridge may be associated with an outer sheath. However, in other exemplary embodiments, a single medical device, and therefore, a single cartridge, or more than two medical devices, and therefore, more than two cartridges, may be used. Accordingly, embodiments wherein more or less than two cartridges are employed remain within the spirit and scope of the present disclosure. Furthermore, as will be described in detail below, medical device form factors other than cartridges 400 may be used with the manipulation assembly 300. In any event, the cartridges (or other medical device form factor) may be coupled, generally speaking, to the RCGS 10 to allow for robotically-controlled movement. In addition to the description set forth herein, further details of a device cartridge can be found in U.S. Patent Publication Nos. 2009/0247943 entitled "Robotic Catheter Device Cartridge" and 2009/0247944 entitled "Robotic Catheter Rotatable Device Cartridge," the entire disclosures of which are incorporated herein by reference.

Figure 2:
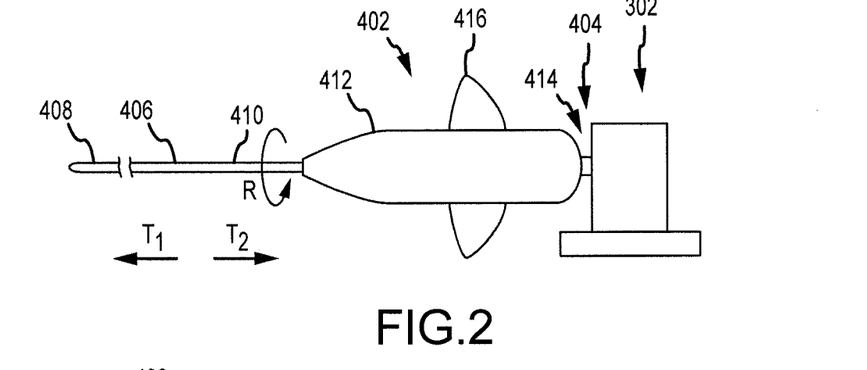
FIG. 2 is a diagrammatic view of an exemplary catheter and catheter manipulation mechanism.

FIG. 2 is a diagrammatic side view of an exemplary catheter 402 and catheter manipulator mechanism 302. The illustrated manipulator mechanism 302 is coupled to the catheter 402 at an interface 404. The catheter 402 can include a shaft 406 with a distal portion 408 and a proximal portion 410 and a handle 412 with a proximal interface 414 and a manual pull wire actuation mechanism 416.

The manipulator mechanism 302 can be configured to translate the catheter 402 generally along the central axis of the catheter 402 in the distal and proximal directions respectively indicated by arrows $T_1$, $T_2$ and, in an embodiment, to rotate the catheter about the central axis of the catheter (as generally indicated by rotation line R). Unlike known robotic systems that manipulate manual catheter handles, the manipulator mechanism 302 may control distal deflection of the catheter by actuating a dedicated actuation mechanism driven through the interface 404, not by actuating the manual pull wire mechanism 416. Such a dedicated remote actuation mechanism is discussed in greater detail in conjunction with FIGS. 3-5. Because the manipulator mechanism controls the deflection of the catheter 402 through an interface 404 that may be used for many different catheters, the manipulator mechanism 302 is capable of use for remote control of many different types of manual catheter handles (given an appropriate configuration, e.g., an interface in the catheter handle). This presents an advantage over known systems, which require different manipulator mechanisms to control different models of catheter handles having different designs.

The catheter 402 can be configured both for manual manipulation by a physician and remote manipulation by the manipulation mechanism 302. Accordingly, the catheter may include a manual pull wire actuation mechanism 416 and a dedicated remote actuation mechanism which, as noted above, is described in further detail in conjunction with FIGS. 3-5. The shape and design of the handle 412, including the manual pull wire actuation mechanism 416, allow a user to manually guide the catheter 402 to an intended location to, e.g., deliver ablation therapy. In addition, the catheter proximal interface 414 provides a functional connection between the catheter 402 and an RCGS for remote guidance and control.

Though not shown, the catheter 402 may include a plurality of electrical components, such as position sensors and other sensors, ablation electrodes, diagnostic electrodes, and the like. Accordingly, the shaft 406 and handle 412 may include signal transmission pathways for signals to and from those electrical components, such as wires and cables, as known in the art. Such transmission pathways may extend from each respective electrical component to the proximal interface 414.

Figure 3:
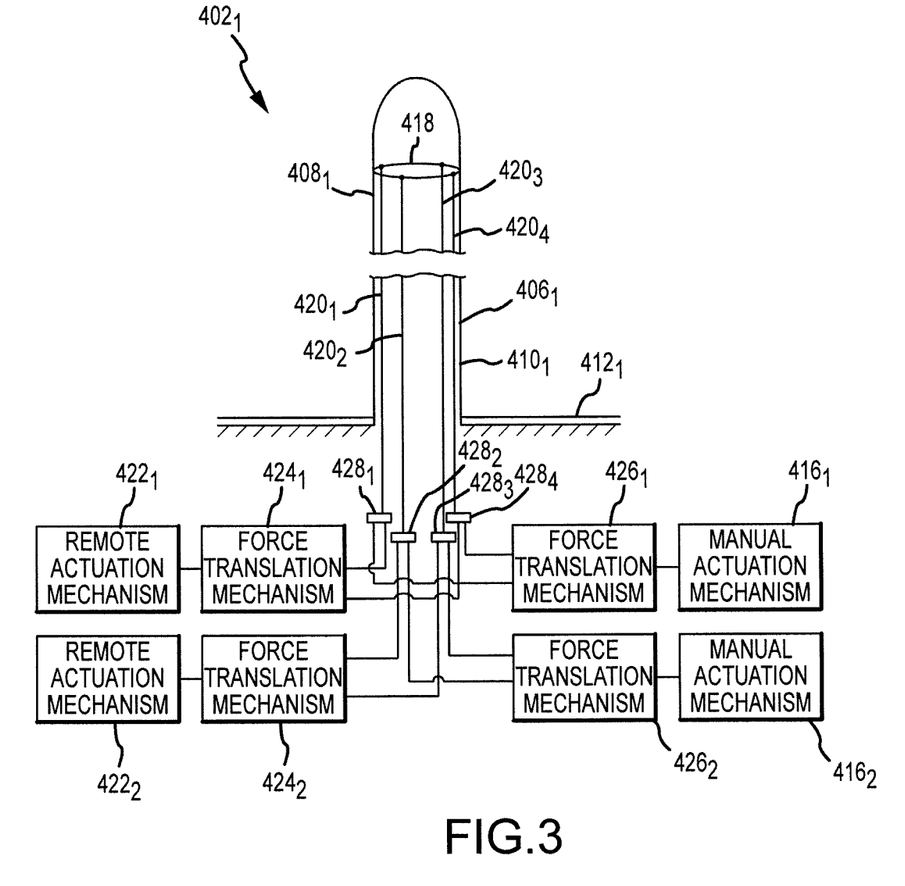
FIG. 3 is a diagrammatic view of an exemplary embodiment of the catheter of FIG. 2.

FIG. 3 is a schematic and block diagram view of an exemplary embodiment of the catheter 402 shown in FIG. 2, designated catheter $402_1$. Illustrated catheter $402_1$ includes a shaft $406_1$ with a distal portion $408_1$, a proximal portion $410_1$, a pull ring 418, and four pull wires 420. The catheter $402_1$ also includes two remote actuation mechanisms 422 coupled to two force translation mechanisms 424, two manual actuation mechanisms 416 coupled to two additional force translation mechanisms 426, and four control elements 428 each respectively coupled to a pull wire 420.

The pull wires 420, pull ring 418, and control elements 428 are provided for deflecting the distal portion $408_1$ of the shaft $406_1$. Each pull wire 420 may be coupled to a control element 428 such that a proximal or distal movement of the control element 428 results in a corresponding proximal or distal movement of the pull wire 420. The movement of the pull wire 420 can be translated into a force on the catheter shaft $406_1$ by the pull ring 418, which in turn can cause the distal portion $408_1$ of the shaft $406_1$ to deflect. In the illustrated embodiment, the four pull wires are provided as two orthogonal pairs, with each wire in a pair effecting a deflection opposite the other wire in the pair. Thus, together the pull wires 420 are configured to deflect the catheter in four directions that are separated by 90 degrees—i.e., the pull wire $420_1$ may effect a deflection to the left in the plane of the page, the pull wire $420_4$ may effect a deflection to the right in the plane of the page, the pull wire $420_3$ may effect a deflection into the page, and the pull wire $420_2$ may effect a deflection out of the page. Though four pull wires 420 are shown, any number of pull wires 420 may be provided in the catheter such as, for example, only two pull wires 420. Additionally, though a pull ring 418 is shown for coupling the pull wires 420 with the catheter shaft $406_1$, the pull wires 420 may be coupled with the catheter shaft through any other means known in the art.

The manual actuation mechanisms 416 can be provided for manual actuation of the pull wires 420 to manually deflect or steer the catheter. Each manual actuation mechanism can be configured to control an opposed pair of pull wires 420—i.e., the first manual actuation mechanism $416_1$ controls the pull wires $428_1$, $428_4$ and the second manual actuation mechanism $416_2$ controls the pull wires $428_2$, $428_3$. The manual actuation mechanisms 416 may comprise mechanisms generally known in the art, such as, for example only, deflection collars on the exterior of the catheter handle $412_1$. Though two manual actuation mechanisms 416 are shown, more or fewer manual actuation mechanisms may be provided. For example, in an embodiment with only two opposed pull wires 420, only one manual actuation mechanism 416 may be provided.

The remote actuation mechanisms 422 can be provided for remote actuation of the pull wires (e.g., by an RCGS) to remotely deflect or steer the catheter $402_1$. If desired, each remote actuation mechanism 422 may be configured to control an opposed pair of pull wires 420—i.e., the first remote actuation mechanism $422_1$ controls the pull wires $428_1$, $428_4$ and the second remote actuation mechanism $422_2$ controls the pull wires $428_2$, $428_3$. The remote actuation mechanisms can be, for example, mechanical, such as sockets (shown in FIGS. 5A-B), rotating rings, or slider blocks, hydraulic (shown in FIG. 4), or another mechanism known in the art.

The force translation mechanisms 424, 426 can be provided to translate a force on an actuation mechanism 416, 422 into a distal or proximal movement of a control element 428 to control the distal deflection of the catheter shaft. The force translation mechanisms 424, 426 may be gears, pulleys, wires, cables, levers, or any other mechanism or combination of mechanisms known in the art. In an embodiment, one or more of the force translation mechanism 424, 426 may be a part of a remote or manual actuation mechanism. Furthermore, like the actuation mechanisms 416, 422, fewer or more force translation mechanisms 424, 426 may be provided depending on the number of pull wires provided in the catheter $402_1$. In addition, the force translation mechanisms 424 for the remote actuation mechanisms 422 and the force translation mechanisms 426 for the manual actuation mechanisms 416 may share components, or may be independent, as shown in FIG. 3.

The control elements 428 can be actuated in pairs—i.e., two control elements that effect deflection in directions 180 degrees opposed to each other can be actuated in tandem by a single actuation mechanism. Accordingly, a single manual actuation mechanism 416 and a single remote actuation mechanism 422 may each be coupled to opposing control elements. For example, in an embodiment, a single deflection collar $416_1$ may be coupled to opposing pull wires $420_1$, $420_4$ via the control elements $428_1$, $428_4$ and the force translation mechanism $426_1$ such that a clockwise turn of the collar $416_1$ results in a proximal force on the control element $428_1$ and a distal force on the other control element $428_4$, while a counter-clockwise turn of the collar does the opposite—i.e., results in a distal force on the control element $428_1$ and a proximal force on the other control element $428_4$. A single remote actuation mechanism $422_1$ may be similarly coupled to the control elements $428_1$, $428_4$ to apply similar opposed forces.

In an alternate embodiment, the catheter $402_1$ may include separate sets of pull wires 420 for actuation by the remote actuation mechanisms 422 and the manual actuation mechanisms 416. Corresponding separate control elements 428 may also be provided. In such an embodiment, the separate sets of pull wires 420 for manual and robotic manipulation may be substantially co-located (i.e., with two pull wires provided adjacent to each other for each deflection direction), or the two separate sets of pull wires may be substantially offset such that the manual actuation mechanisms 416 and the remote actuation mechanisms 422 deflect the catheter in different directions.

Figure 4:
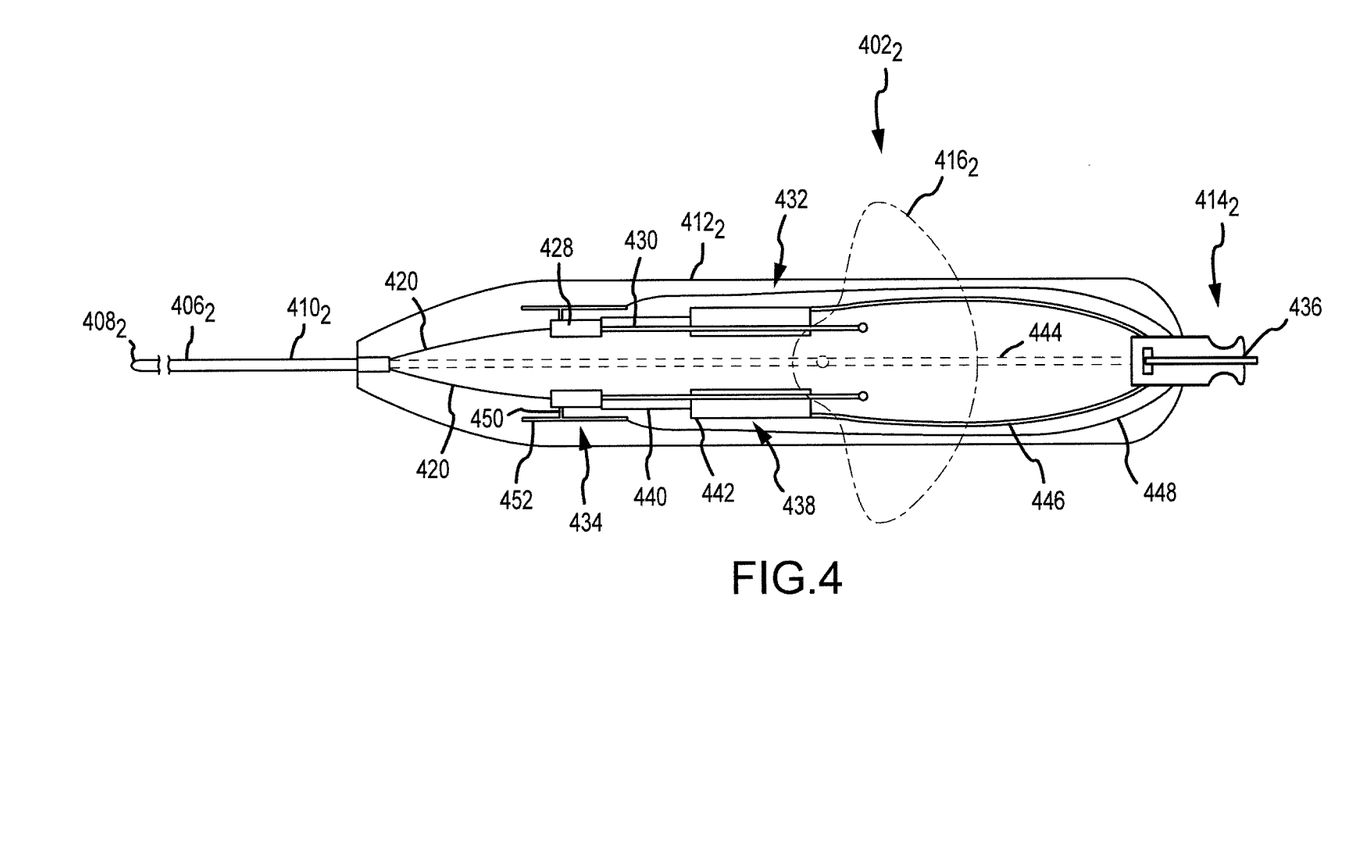
FIG. 4 is a diagrammatic view of an exemplary embodiment of the catheter of FIG. 2.

FIG. 4 is a diagrammatic view of the interior of an exemplary embodiment of the catheter 402 of FIG. 2, designated catheter $402_2$. The catheter $402_2$ includes a shaft $406_2$ having a distal portion $408_2$ and a proximal portion $410_2$, and a handle $412_2$ including a manual actuation mechanism $416_2$ (shown in phantom), an irrigation fluid pathway 444 (also shown in phantom), a proximal interface $414_2$ with a shunt valve 436, two pull wires 420, a control element 428 (shown as an anchor block) for each pull wire, a mechanical drive link 430 for each pull wire, a hydraulic system 432, and a pull wire position sensor 434 for each pull wire. The illustrated hydraulic system 432 includes a hydraulic drive 438 for each pull wire, each hydraulic drive 438 including a drive shaft 440, a hydraulic cylinder 442, and a hydraulic fluid line 446.

Each anchor block control element 428 may be rigidly coupled to a respective pull wire 420, but can be movably disposed in the catheter $402_2$. Thus, a movement of an anchor block control element 428 may result in a movement of a pull wire 420 and a deflection of the distal portion $408_2$ of the shaft $406_2$. As noted above with respect to FIG. 3, the anchor block control elements 428 may be actuated or controlled in tandem, such that a proximal force on one anchor block may be accompanied by a distal force on the other anchor block.

The catheter $402_2$ may be designed for both manual manipulation by a user and remote manipulation with an RCGS. Accordingly, the exterior of the handle $412_2$ and the manual actuation mechanism $416_2$ can be designed for manual manipulation by a user in a fashion similar to known manual catheter handles. The manual actuation mechanism $416_2$ can be, as noted above, any manual actuation mechanism known in the art. The manual actuation mechanism $416_2$ can be coupled to each anchor block 428 through a mechanical link 430 (analogous to a force translation mechanism 426 shown in FIG. 3), such that rocking the manual actuation mechanism $416_2$ in a chosen direction can result in opposed respective proximal and distal forces on the two anchor blocks 428 (and thus, on the two pull wires 420).

The hydraulic system 432 may be provided in the catheter as a remote mechanism for pull wire actuation by an RCGS. In the hydraulic system 432, hydraulic fluid flows through the fluid lines 446 to actuate the drive cylinders 442 (i.e., to move a piston in the hydraulic cylinder 442 towards the proximal or distal end of the catheter handle). Each drive cylinder 442 can actuate a respective drive shaft 440, which may be coupled to a respective anchor block control element 428. Thus, a proximal or distal movement of a piston in a hydraulic drive cylinder 442 results in a corresponding proximal or distal force on an anchor block control element 428.

The pull wire position sensors 434 can assist with determining the position of the pull wires 420 so that, for example only, a mapping and positioning system may accurately determine the degree of deflection (and, thus, the overall shape) of the distal portion $408_2$ of the catheter shaft $406_2$. Each position sensor 434 is shown as a potentiometer, though other position sensing devices may be used, such as a linear variable differential transformer (LVDT), a Bragg grating, or another device based on optic methods, such as interferometry or reflectance.

Each potentiometer 434 includes a wiper 450 movable relative to a resistive track 452. In an embodiment, the wiper 450 can be rigidly coupled to the anchor block control element 428. As the anchor block control element 428 (and, thus, the wiper 450) moves proximally or distally, the wiper's position on the resistive track 452 changes. As the position of the wiper 450 changes, so does the electrical resistance of the resistive track 452. By applying an electrical signal through the resistive track 452, the RCGS can measure the resistance of the resistive track 452 to determine the position of the anchor block control element 428 at any given time and estimate the shape of the shaft distal portion $408_2$ accordingly. Such an electrical signal may be carried between the interface $414_2$ and the position sensor 434 by a signal cable 448, which may be any appropriate electrical cable or wiring known in the art.

As noted above, the catheter $402_2$ also includes a proximal interface $414_2$ that may function as the sole interface between the catheter $402_2$ and an RCGS, including mechanical, electrical, and fluid coupling. Accordingly, the proximal interface $414_2$ may include a shunt valve 436 that allows hydraulic fluid to circulate freely in the hydraulic system 432 when the catheter $402_2$ is not connected to a RCGS (and thus, prevents the pistons in the drive cylinders 442 from opposing forces applied through the manual actuation mechanism $416_2$), but permits a fluidic connection between the manipulation mechanism 302 and the hydraulic fluid lines 446 so that the RCGS may drive the hydraulic system 432 as a remote manipulation mechanism. Thus, when the catheter $402_2$ is connected to the manipulation mechanism 302 via the proximal interface $414_2$, the RCGS can drive the hydraulic system 432 with hydraulic elements (e.g., drive cylinders, drive shafts) included in the manipulation mechanism 302 or elsewhere in the RCGS. The proximal interface $414_2$ may also include electrical connections and mechanical coupling for the manipulator mechanism 302, examples of which are shown in FIGS. 5A-5B.

Figure 5A:
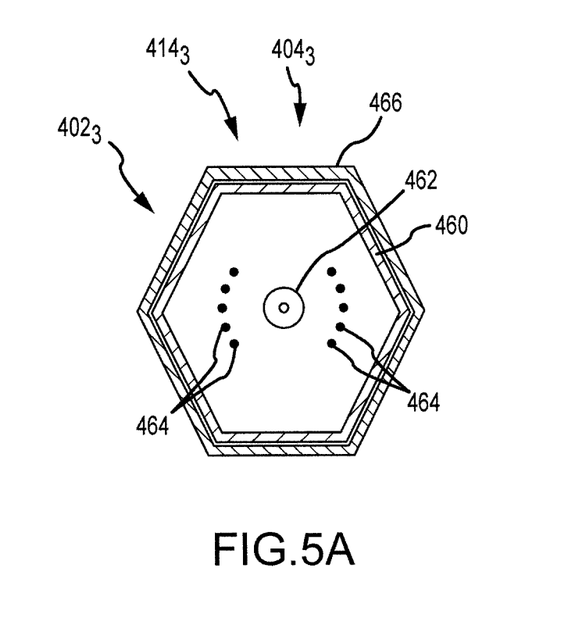
FIGS. 5A-5B are cross-sectional views of exemplary interfaces between the catheter and the catheter manipulation mechanism of FIG. 2.
Figure 5B:
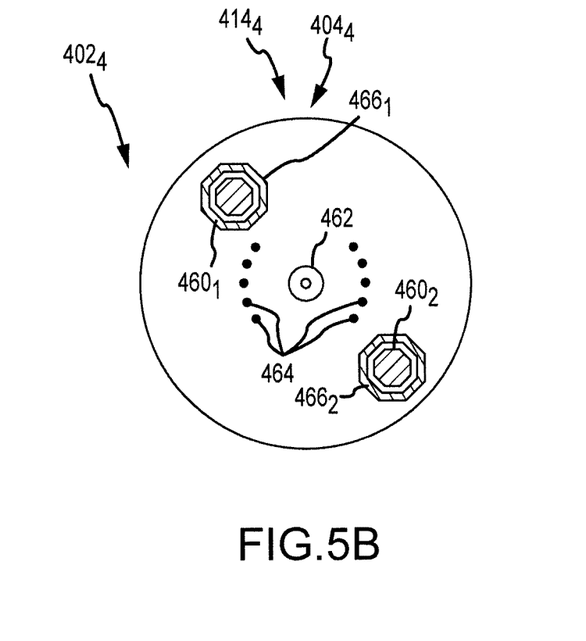

FIGS. 5A and 5B illustrate exemplary embodiments an interface 404 between a catheter 402 and a manipulator mechanism 302.

FIG. 5A is a partial cross-sectional view of an exemplary embodiment of an interface $404_3$ between an exemplary embodiment of a catheter $402_3$ and the manipulation mechanism 302. The illustrated interface $404_3$ includes elements from a proximal interface $414_3$ of an exemplary catheter $402_3$ and elements from the connection port of the manipulation mechanism 302. The proximal interface $414_3$ of the catheter $402_3$ includes a remote actuation mechanism (shown as an interior socket 460), an irrigation fluid port 462, and electrical connections 464. The connection port of the manipulation mechanism 302 includes an exterior socket 466 and complementary components for the fluid line and electrode connections.

The irrigation fluid port 462 is provided for the flow of irrigation fluid from the manipulation mechanism 302 to the catheter $402_3$. Irrigation fluid may be provided to the distal portion of the catheter $402_3$ to, for example, prevent the buildup of coagulum at an ablation site and/or to reduce the temperature of an ablation electrode. Irrigation fluid may be provided by a fluid pump or saline drip in the RCGS (not shown), and may flow through a fluid lumen in the catheter $402_3$, such as, for example only, the fluid lumen 444 shown in FIG. 4.

The electrical connections 464 can provide signal pathways for signals to or from one or more sensors, electrodes, or other components disposed in the catheter $402_3$, such as, for example, positioning sensors, ablation electrodes, mapping electrodes, and the like. Although ten electrode connections 464 are provided in the interface $414_3$, not all are designated for visual clarity. More or fewer electrode connections may be provided as needed, depending on the configuration of the catheter $402_3$.

The interior socket 460 may be configured both for mechanically coupling the catheter $402_3$ with the manipulation mechanism 302 and as a remote actuation mechanism. A clockwise turn of the exterior socket 466 of the manipulation mechanism 302 (controlled by the RCGS as described above in conjunction with FIG. 1) may impart a clockwise force on the interior socket 460, which in turn may be translated into a force on the pull wires 420 of the catheter $402_3$ by a force translation mechanism 424 (not shown in FIG. 4A) to deflect or steer the distal portion of the catheter $402_3$. As noted above, the force translation mechanism 424 may include gears, pulleys, wires, cables, levers, or any other mechanism or combination of mechanisms known in the art.

FIG. 5B is a partial cross-sectional view of an exemplary embodiment of an interface $404_4$ between an exemplary embodiment of a catheter $402_4$ and the manipulation mechanism 302. The interface $404_4$ includes the same fluid port 462 and electrical connections 464 as the interface $404_3$ shown in FIG. 5A. Accordingly, the description of those components set forth above may apply equally to the interface $404_4$ and the catheter $402_4$. The interface $404_4$ may also include two socket connections, each including an interior socket 460 configured to interact with an exterior socket 466 disposed in the manipulation mechanism 302.

Each of the interior sockets may be used as a remote manipulation mechanism to actuate opposing control elements and opposing pull wires (as shown in FIG. 3). Thus, each interior socket may be respectively coupled with a force translation mechanism 424 to control two pull wires 420. With two sockets, the interface $404_4$ may be used to control the movement of a catheter with four pull wires. In an embodiment, two sockets may also be included on a catheter with only two pull wires—the first socket as an actuation means for the two pull wires, and the second socket only as a means of mechanical coupling.

A catheter with a first, manual manipulation mechanism and a second, remote manipulation mechanism as described above can provide advantages over known catheters and devices used in remote systems. First, the same catheter may be used both for manual and remote manipulation without sacrificing manual or remote control quality. Second, the same robotic manipulator may be used to control many different types of catheters, without regard for the placement and design of manual actuation mechanisms, given a proper interface on the catheter.

A second way of improving on known catheters for remote manipulation is with a modular catheter cartridge that can be coupled with an RCGS or with a manual catheter handle portion designed for use with the modular cartridge.

Figure 6:
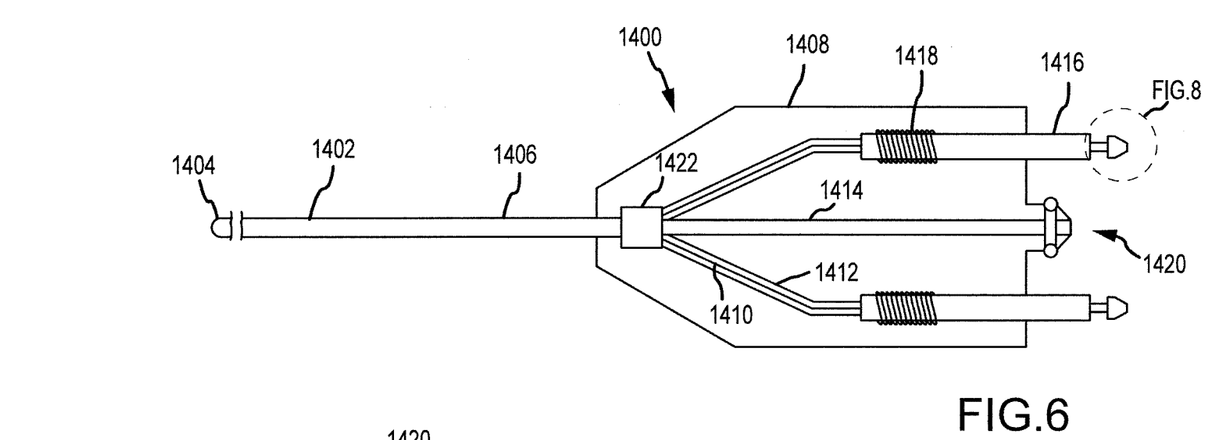
FIG. 6 is a diagrammatic view of an exemplary embodiment of a modular catheter cartridge.

FIG. 6 is a diagrammatic view of the interior of a modular catheter cartridge 1400 that can be coupled with either an RCGS or with a catheter handle portion for manual manipulation by a physician. The illustrated cartridge 1400 includes a catheter shaft 1402 having a distal portion 1404 and a proximal portion 1406, a housing 1408, two pull wires 1410 respectively disposed in two pull wire channels 1412, an irrigation fluid lumen 1414, two interface pins 1416, two interface pin position sensors 1418, and a proximal interface 1420. The proximal portion 1406 of the shaft 1402 is coupled to the housing 1408 by an anchor block 1422.

The pull wires 1410 may extend to the distal portion 1404 of the shaft 1402 and may be coupled with the shaft 1402 with, for example only, a pull ring, as shown in FIG. 3. As described above, each pull wire may be used to deflect the distal portion 1404 by applying a distal or proximal force to the pull wire.

Each pull wire 1410 can be coupled with a respective interface pin 1416 which is movably coupled with the housing 1408. Each interface pin 1416 may act as a control element for a pull wire 1412, such that proximal or distal movement of an interface pin 1416 results in deflection of the distal portion 1404 of the catheter shaft 1402. As a result, the interface pins 1416 may be moved proximally and distally by an RCGS or by a manual catheter handle portion to deflect the distal portion 1404 of the catheter shaft 1402. It should be understood that the interface pins 1416 need not take the form shown in FIG. 6—e.g., the interface pins 1416 may extend proximally from the housing 1408, as shown, or may be contained entirely within the housing 1408, and may have any appropriate shape and size.

Each interface pin 1416 may be coupled with a respective interface pin position sensor, shown as a linear variable differential transformer (LVDT) 1418. Each LVDT 1418 can determine the position of an interface pins 1416, and thus can determine the tension on each pull wire 1410 to estimate the shape of the distal portion 1404 of the catheter shaft 1402. The LVDT 1418 may function as known in the art. In an embodiment, a center coil of the LVDT 1418 may be rigidly coupled to the interface pin 1416, while two secondary coils may be movable relative to the interface pin 1416. A current may be driven through the center coil, and the current induced on the secondary coils by the primary coil current may be measured. The secondary coils may be wound and positioned such that, in a balanced state (i.e., when the interface pin 1416 is in a neutral position), the currents induced on the two secondary coils are equal and opposite. However, when the primary coil moves from a neutral position, an unequal current is induced on the two secondary coils. The position of the center coil, and thus of the interface pin, may thus be determined based on the currents in the secondary coils. Of course, other position sensing means may be used, such as a potentiometer, as described above, or another position sensor as known in the art.

The modular catheter cartridge 1400 may be coupled to either an RCGS for remote control (i.e., similarly to cartridges in known robotic systems) or to a manual handle for manual manipulation by a physician. Accordingly, the housing 1408 can be configured in size and shape to resemble the distal end of a traditional manual catheter handle. In an embodiment, the housing 1408 may be substantially round (i.e., may have a substantially round cross-section taken transverse to the plane of the page).

The fluid lumen 1414 may provide for the flow of irrigation fluid to the distal portion 1404 of the catheter shaft 1402. As noted above, irrigation fluid may be provided to cool an ablation electrode and/or to prevent the buildup of coagulum at an ablation site.

Though not shown, the catheter shaft 1402 may include a plurality of electrical components, such as position sensors and other sensors, ablation electrodes, diagnostic electrodes, and the like. Accordingly, the shaft 1402 and housing 1408 may include signal transmission pathways for signals to and from those electrical components, such as wires and cables, as known in the art. Such transmission pathways may extend from each respective electrical component to the proximal interface 1420. Similar transmission pathways may be provided for the interface pin position sensors 1418.

Figure 7:
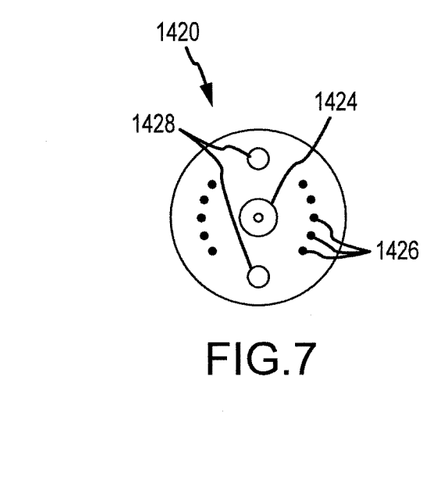
FIG. 7 is an end view of the fluid and electrical interface of the modular catheter cartridge of FIG. 6.

FIG. 7 is an end view of the proximal interface 1420. The proximal interface 1420 may include an irrigation fluid port 1424 for fluid access to the fluid lumen 1414, a plurality of electrical connections 1426 for access to the transmission pathways of the LVDTs 1418 as well as other sensors, electrodes, and electrical components, and mechanical interlock ports 1428 for securely coupling the modular cartridge 1400 with either a manual handle portion or with an RCGS manipulator.

Figure 8:
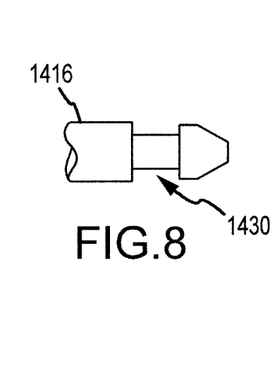
FIG. 8 is an enlarged view of a portion of FIG. 6, generally illustrating the mechanical locking mechanism of the catheter cartridge.

FIG. 8 is an enlarged view of the proximal end of an interface pin 1416. The interface pin 1416 includes a detent 1430 configured for mechanical coupling with an RCGS manipulator or with a manual catheter handle portion.

It should be understood that the number of pull wires and interface pins shown for the modular catheter cartridge 1400 is exemplary only, and not limiting. The modular catheter cartridge 1400 may be provided with more or fewer pull wires and a corresponding number of interface pins such as, for example only, four pull wires and four interface pins, and remain within the spirit and scope of the present invention.

Figure 9:
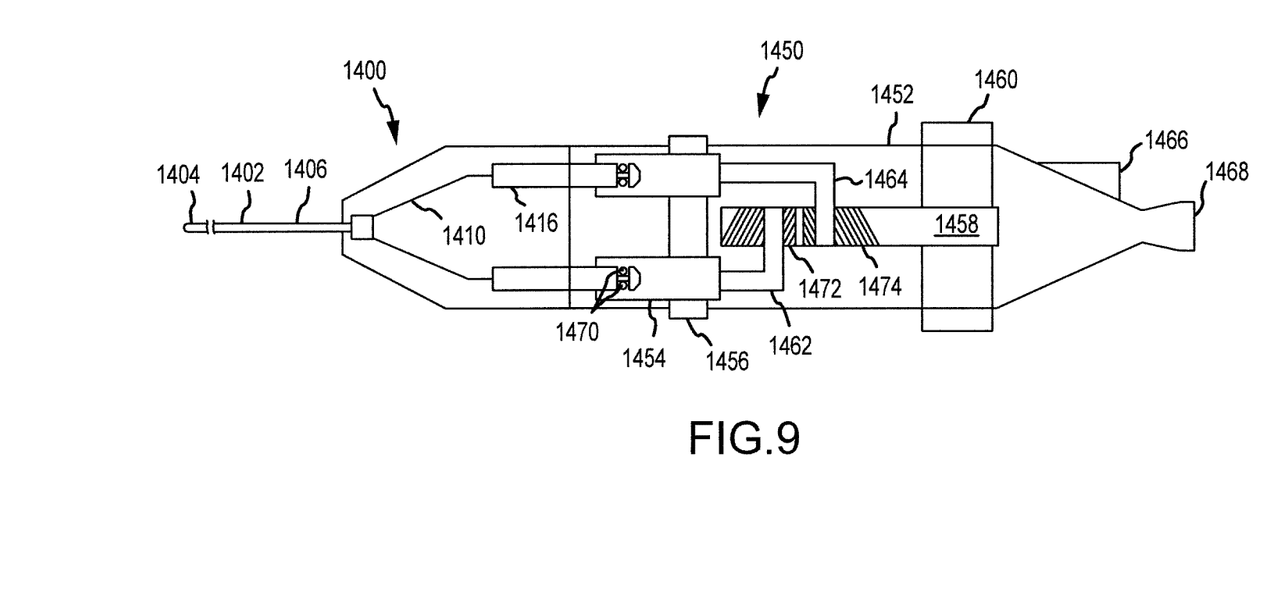
FIG. 9 is a diagrammatic view of a modular catheter cartridge, such as generally illustrated in FIG. 6, shown coupled with a modular catheter handle.

FIG. 9 is a diagrammatic view of an embodiment of the interior of the modular catheter cartridge 1400 (with portions omitted for visual clarity) and a manual handle portion 1450 coupled to the modular cartridge 1400. The illustrated manual handle portion 1450 includes a housing 1452, two receiving blocks 1454, an interface pin release 1456, a differential lead screw 1458, a manual actuation mechanism 1460, two slides 1462, 1464, an electrical connection interface 1466, and a fluid connection interface 1468.

Each of the receiving blocks 1454 can be configured to receive a respective interface pin 1416. Accordingly, each receiving block 1454 may include two engagement pins 1470 configured to engage the detent 1430 in the interface pin 1416. The engagement pins 1470 can be coupled to the interface pin release 1456 such that depressing the interface pin release 1456 removes the engagement pins 1470 from the detent 1430, and the interface pin 1416 can be removed.

Each receiving block 1454 may be rigidly coupled with a slide 1462, 1464 and the receiving blocks 1454 and slides 1462, 1464 can be movable relative to the housing 1452. As a result, when the interface pins 1416 are coupled with the receiving blocks 1454, distal and proximal translation of the receiving blocks 1454 can result in distal and proximal force on the pull wires 1410 and deflection of the distal portion 1404 of the catheter shaft 1402.

Translational movement of the receiving blocks 1454 can be provided by the differential lead screw 1458. The differential lead screw 1458 may include a first section 1472, coupled with the first slide 1462, with right-handed windings and a second section 1474, coupled with the second slide 1464, with left-handed windings. The first and second slide 1462, 1464 have windings compatible with the lead screw sections 1472, 1474 such that rotation of the lead screw 1458 translates the slides 1462, 1464 (and, as a result, the receiving blocks 1454) in opposite directions (i.e., one proximally and the other distally). A clockwise movement of the lead screw 1458 may translate the first slide 1462 in the proximal direction and the second slide 1464 in the distal direction. A counter-clockwise movement of the lead screw 1458 may translate the first slide 1462 in the distal direction and the second slide 1464 in the proximal direction.

The lead screw 1458 may be coupled to the manual actuation mechanism 1460 such that rotation of the manual actuation mechanism 1460 rotates the lead screw 1458. As a result, the manual actuation mechanism 1460 can be used for manual deflection of the catheter shaft 1402. In an embodiment, the manual actuation mechanism 1460 may be a deflection collar. In the embodiment, a clockwise turn of the deflection collar would result in a corresponding clockwise rotation of the lead screw 1458 and proximal and distal movement of the receiving blocks 1454 and deflection of the catheter shaft 1402.

As noted above, irrigation fluid may be provided to the distal portion 1404 of the shaft 1402 via a fluid port 1424 in the modular cartridge proximal interface 1420. The handle portion 1450 may also include a fluid lumen that extends from fluid port 1424 of the proximal interface 1420 of the catheter cartridge 1400 to the fluid interface 1468 of the handle portion 1450. An irrigation fluid pump or other source of irrigation fluid may thus provide irrigation fluid for the catheter through the handle portion fluid interface 1468.

Also as noted above, the modular catheter cartridge 1400 may include a number of electrical components, such as sensors and other electrodes. The handle portion 1450 may include transmission pathways extending from the electrical connections 1426 in the modular cartridge proximal interface 1420 to the handle portion electrical interface 1466. Thus, one or more systems may be connected to the electrical components of the modular cartridge 1400, such as, for example only, a mapping and navigation system, such as the ENSITE VELOCITY system described above, or an ablation system.

The modular catheter cartridge 1400 may also be coupled with an RCGS having a manipulator with components similar to those in the handle portion 1450—i.e., receiving blocks, a mechanism for translating the receiving blocks, and fluid and electrical interfaces. Accordingly, the modular catheter cartridge may be controlled manually (through the use of a corresponding manual handle, such as the handle portion 1450) or remotely with an RCGS.

Although numerous embodiments of this invention have been described above with a certain degree of particularity, those skilled in the art could make numerous alterations to the disclosed embodiments without departing from the spirit or scope of this invention. All directional references (e.g., plus, minus, upper, lower, upward, downward, left, right, leftward, rightward, top, bottom, above, below, vertical, horizontal, clockwise, and counterclockwise) are only used for identification purposes to aid the reader's understanding of the present invention, and do not create limitations, particularly as to the position, orientation, or use of the invention. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the spirit of the invention as defined in the appended claims.

What is claimed is:

1. An elongate medical device comprising:
   a shaft having a proximal portion and a distal portion;
   a pull wire disposed in said shaft and affixed to said distal portion of said shaft; and a handle having a distal end and a proximal end, said distal end coupled with the proximal portion of said shaft and said proximal end opposite said distal end, said handle comprising:
- a first mechanism configured for manual actuation of said pull wire so as to deflect the distal portion of said shaft;
- a second mechanism configured for remote actuation of said pull wire so as to deflect the distal portion of said shaft; and
- a mechanical interface disposed at said proximal end of said handle and configured to provide a remote system with a functional connection to said second mechanism.

2. The elongate medical device of claim 1, wherein said second mechanism is a hydraulic mechanism.

3. The elongate medical device of claim 2, wherein said hydraulic mechanism comprises:
- a drive cylinder;
- a hydraulic fluid line coupled at a first end of said fluid line with said drive cylinder and at a second end of said fluid line with said interface, said fluid line configured to provide fluid to said drive cylinder; and
- a drive shaft coupled with said drive cylinder;
- wherein said drive shaft is coupled to said pull wire through an anchor block.

4. The elongate medical device of claim 3, wherein said mechanical interface comprises:
- a hydraulic fluid port coupled with said hydraulic fluid line; and
- a valve configured to selectively permit said remote system access to said hydraulic fluid line or to seal said hydraulic fluid line.

5. The elongate medical device of claim 3, wherein said first mechanism is coupled to said pull wire through said anchor block.

6. The elongate medical device of claim 1, further comprising a force translation mechanism configured to translate force on said second mechanism into actuation of said pull wire.

7. The elongate medical device of claim 6, wherein said force translation mechanism comprises one or more mechanisms selected from the group consisting of:
- gears;
- pulleys;
- wires;
- cables; and
- levers.

8. The elongate medical device of claim 6, wherein said second mechanism comprises a rotatable socket.

9. The elongate medical device of claim 8, wherein said pull wire is a first pull wire configured to deflect said distal portion in a first deflection direction in response to torque on said socket in a first rotational direction, said medical device further comprising a second pull wire configured to deflect said distal portion in a second deflection direction opposite said first deflection direction in response to torque on said socket in a second rotational direction opposite said first rotational direction.

10. The elongate medical device of claim 9, wherein said socket is a first socket, further comprising:
- a third pull wire and a second socket coupled to said third pull wire;
- wherein said third pull wire is configured to deflect said distal portion in a third deflection direction substantially orthogonal to said first and second directions in response to torque on said second socket.

11. The elongate medical device of claim 1, further comprising a sensor configured to determine the position of said pull wire.

12. The elongate medical device of claim 1, further comprising an irrigation fluid pathway extending through said shaft and terminating at an irrigation fluid port in said mechanical interface.

13. An elongate medical device comprising:
- a modular cartridge comprising:
  - a housing;
  - a shaft having a distal portion and a proximal portion, said proximal portion coupled with said housing;
  - a pull wire extending through said shaft and coupled with said distal portion of said shaft; and
  - an interface member movably disposed within said housing, said interface member coupled with said pull wire such that movement of said interface member results in movement of said pull wire;
  - a connection interface comprising at least one electrical connection; and
- a handle portion releasably coupled to said modular cartridge, comprising:
  - a receiving member releasably coupled with said interface member; and
  - an actuation mechanism configured for manual manipulation, coupled with said receiving member, configured to impart force to said pull wire through said receiving member so as to deflect the distal portion of said shaft.

14. The elongate medical device of claim 13, wherein said modular cartridge connection interface further comprises an irrigation fluid port.

15. The elongate medical device of claim 14, wherein said at least one electrical connection is for electrically coupling said handle portion with a sensor disposed in said shaft.

16. The elongate medical device of claim 15, wherein said handle portion further comprises:
- a handle portion fluid interface; and
- a handle portion electrical interface.

17. The elongate medical device of claim 13, wherein said modular cartridge housing is substantially round.

18. The elongate medical device of claim 13, wherein said modular cartridge further comprises a sensor configured to sense the position of said interface member.

19. An elongate medical device comprising:
- a shaft having a proximal portion and a distal portion;
- a pull wire disposed in said shaft and affixed to said distal portion of said shaft; and
- a handle having a distal end and a proximal end, said proximal end opposite said distal end said proximal portion of said shaft extending from said distal end, said proximal end comprising an interface for coupling with a remote catheter guidance system, said interface comprising at least one electrical connector, a fluid port, a mechanical interlock, and an apparatus for actuating said pull wire so as to deflect said distal portion of said shaft.

20. The elongate medical device of claim 19, wherein said apparatus for actuating said pull wire comprises one or more of a hydraulic fluid port and a socket.

* * * * *